(12) United States Patent
Vesely et al.

(10) Patent No.: US 7,769,439 B2
(45) Date of Patent: Aug. 3, 2010

(54) BRAIN BALANCING BY BINAURAL BEAT

(75) Inventors: Michael A. Vesely, Santa Cruz, CA (US); Nancy Clemens, Santa Cruz, CA (US)

(73) Assignee: Infinite Z, Inc., Campbell, CA (US)

( * ) Notice: Subject to any disclaimer, the term of this patent is extended or adjusted under 35 U.S.C. 154(b) by 1047 days.

(21) Appl. No.: 11/292,376

(22) Filed: Nov. 28, 2005

(65) Prior Publication Data

US 2006/0116597 A1 Jun. 1, 2006

Related U.S. Application Data

(60) Provisional application No. 60/632,085, filed on Nov. 30, 2004.

(51) Int. Cl.
*A61B 5/04* (2006.01)
(52) U.S. Cl. ................................ 600/544; 600/545
(58) Field of Classification Search ............. 600/544, 600/545
See application file for complete search history.

(56) References Cited

U.S. PATENT DOCUMENTS

| | | | |
|---|---|---|---|
| 3,753,433 A * | 8/1973 | Bakerich et al. | 600/545 |
| 3,831,949 A | 8/1974 | Henning | |
| 3,978,847 A | 9/1976 | Fehmi et al. | |
| 4,031,883 A | 6/1977 | Fehmi et al. | |
| 4,493,327 A | 1/1985 | Bergelson et al. | |
| 5,003,986 A | 4/1991 | Finitzo et al. | |
| 5,036,858 A * | 8/1991 | Carter et al. | 600/545 |
| 5,135,468 A | 8/1992 | Meissner | |
| 5,213,562 A * | 5/1993 | Monroe | 600/28 |
| 5,280,793 A | 1/1994 | Rosenfeld | |
| 5,282,475 A | 2/1994 | Urbach et al. | |
| 5,356,368 A * | 10/1994 | Monroe | 600/28 |
| 5,365,939 A * | 11/1994 | Ochs | 600/545 |
| 5,450,855 A | 9/1995 | Rosenfeld | |
| 5,740,812 A | 4/1998 | Cowan | |
| 6,052,619 A | 4/2000 | John | |
| 6,081,743 A * | 6/2000 | Carter et al. | 600/544 |
| 6,385,486 B1 | 5/2002 | John et al. | |
| 6,431,705 B1 | 8/2002 | Linden | |

(Continued)

FOREIGN PATENT DOCUMENTS

GB 2396421 A 6/2004

OTHER PUBLICATIONS

US International Searching Authority; International Search Report and Opinion for PCT/US2006/17597; Sep. 20, 2006; US.

(Continued)

*Primary Examiner*—Patricia C Mallari
*Assistant Examiner*—Karen E Toth
(74) *Attorney, Agent, or Firm*—Fish & Richardson P.C.

(57) ABSTRACT

A method and apparatus to balance the brain left side and the brain right side by using binaural beat is disclosed. The disclosed apparatus comprises an electroencephalographic (EEG) system to measure the brain left and right electrical signals, and an audio generator to generate a binaural beat to compensate for the unbalanced EEG frequencies. The disclosed method includes measuring the brain wave frequency spectrum of the individual, selecting the frequency exhibiting imbalanced behavior, and generating a binaural beat of that frequency. The binaural beat can be continuous or intermitten.

19 Claims, 1 Drawing Sheet

U.S. PATENT DOCUMENTS

| | | |
|---|---|---|
| 7,471,978 B2 | 12/2008 | John et al. |
| 2004/0002635 A1 | 1/2004 | Hargrove et al. |
| 2006/0116597 A1 | 6/2006 | Vesely et al. |
| 2006/0116598 A1 | 6/2006 | Vesely et al. |
| 2007/0040905 A1 | 2/2007 | Vesely et al. |
| 2007/0043466 A1 | 2/2007 | Vesely et al. |

OTHER PUBLICATIONS

US International Searching Authority; International Search Report and Opinion for PCT/US2006/17597; mailed Sep. 20, 2006, 9 pages.

USPTO First Office Action in U.S. Appl. No. 11/292,382, mailed Nov. 23, 2009, 13 pages.

* cited by examiner

BRAIN BALANCING BY BINAURAL BEAT

This application claims priority from U.S. provisional applications Ser. No. 60/632,085, filed Nov. 30, 2004, entitled "Brain Balancing by Binaural Beat", which is incorporated herein by reference.

FIELD OF INVENTION

The present invention relates generally to methods and apparatus for balancing brain wave frequencies, and more particularly, to modification of the state of being of the human brain by use of an audio signal.

BACKGROUND OF THE INVENTION

The living brains exhibits electrical activity, which vary in strength and frequency over time and from one part of the brain to another. Different frequencies are associated with different moods and changing abilities. A brain wave frequency of 13 hertz or higher is known as "beta-rhythm" and is normally associated with daily activity when all five sensory organs are functioning. A brain wave frequency of 8 to 13 hertz is known as "alpha-rhythm" and is often associated with a relaxed creative state. Brain wave frequencies of 4 to 8 hertz and 0.5 to 4 hertz are known as "theta-rhythm" and "delta-rhythm" respectively. Theta-rhythm is often found in adolescents with learning disorders, and delta-rhythm is typical of normal sleep. Researchers believe that externally creating brain wave frequencies associated with normal or desired behavior, such as externally creating delta-rhythm in someone who has a problem sleeping or alpha-rhythm in someone who has trouble learning, can help bring about such behavior.

Alpha waves are those between 7.5 and thirteen (13) waves per second (Hz). Alpha is usually best seen in the posterior regions of the head on each side, being higher in amplitude on the dominant side. It is brought out by closing the eyes and by relaxation, and abolished by eye opening or alerting by any mechanism (thinking, calculating). It is the major rhythm seen in normal relaxed adults—it is present during most of life especially beyond the thirteenth year when it dominates the resting tracing.

Beta activity is 'fast' activity. Its frequency is 14 Hz and higher. It is usually seen on both sides in symmetrical distribution and is most evident frontally. It is accentuated by sedative-hypnotic drugs especially the benzodiazepines and the barbiturates. It may be absent or reduced in areas of cortical damage. It is generally regarded as a normal rhythm. It is the dominant rhythm in patients who are alert or anxious or who have their eyes open.

Theta activity has a frequency of 3.5 to 7.5 Hz and is classed as "slow" activity. It is abnormal in awake adults but is perfectly normal in children up to 13 years and in sleep. It can be seen as a focal disturbance in focal subcortical lesions; it can be seen in generalized distribution in diffuse in diffuse disorder or metabolic encephalopathy or deep midline disorders or some instances of hydrocephalus Delta activity is 3 Hz or below. It tends to be the highest in amplitude and the slowest waves. It is quite normal and is the dominant rhythm in infants up to one year and in stages 3 and 4 of sleep. It may occur focally with subcortical lesions and in general distribution with diffuse lesions, metabolic encephalopathy hydrocephalus or deep midline lesions. It is usually most prominent frontally in adults and posteriorly in children.

One of the first "brain scan", the EEG, or electroencephalograph, is still very useful in non-invasively observing the human brain activity. An EEG is a recording of electrical signals from the brain made by hooking up electrodes to the subject's scalp, typically placed on the head in the standard ten-twenty configuration. These electrodes pick up electric signals naturally produced by the brain and send them to galvanometers (amperemeter) that are in turn hooked up to pens, under which graph paper moves continuously. The pens trace the signals onto the graph paper. Modern EEG equipment now uses electronics, such as computer, to store the electric signals instead of using pens and graph papers.

EEGs allow researchers to follow electrical impulses across the surface of the brain and observe changes over split seconds of time. An EEG can show what state a person is in—asleep, awake, anaesthetized—because the characteristic patterns of current differ for each of these states. One important use of EEGs has been to show how long it takes the brain to process various stimuli.

The electrical activity, or EEG, of human brains has traditionally been used as a diagnostic marker for abnormal brain function and related symptomatic dysfunction. Often, traumatic disturbances such as mechanical injury, social stress, emotional stress and chemical exposure cause neurophysiological changes that will manifest as EEG abnormalities. However, disruption of this abnormal EEG activity by the application of external electrical energy, henceforth referred to as a neurostimulation signal, may cause yet further neurophysiological changes in traumatically disturbed brain tissues, as evidenced in an amelioration of the EEG activity, and hence are beneficial to an individual. Such therapeutic intervention has proven useful in pain therapy and in treating a number of non-painful neurological deficits such as depression, attention deficit disorder, and many others.

Therefore, the need and desire is very strong and there has been a great search for techniques and external stimuli which can vary the brain state. Much has been written about the benefits of relaxation and stress reduction. Stress has been shown to contribute to heart attacks, and is known to suppress the normal operation of the immune system, thus leaving the body vulnerable to attack from many serious illnesses. Different approaches have been made with respect to varying the brain state of a person. For example, various audio systems are commercially sold using subliminal messages in order to coax the brain into a different state.

There are known consciousness state inducing techniques. For example the use of audio generators to induce a state of consciousness known as sleep. In one type of technique exemplified in these patents, generated audio signals include pleasing and harmonious study sounds or vibrations, fixed frequency signals which are buried cyclically with respect to amplitude, and repetitive sounds such as the falling of rain on the roof and the sighing wind through the trees.

There is a method of inducing sleep by generation of an audible or tactual signal which is related to the physiological process of heartbeat and respiration. In this method, the pitch and amplitude of a pleasing audio signal are varied at a rate somewhat slower than either the rate of heartbeat or the rate of respiration. As a result, heartbeat and respiration tend to synchronize with the audio signal, thus lowering heartbeat and respiration rates and inducing sleep.

Of course, there are other naturally-occurring sounds which have been recorded, and which are not varied, but which instead induce a state of relaxation which leads to sleep for a similar reason. For example, the pounding of waves on a shore line occurs at a frequency generally lower than that of heartbeat or respiration, and induces a state of relaxation.

It is indicated that a beat frequency can be produced inside of the brain by supplying signals of different frequencies to the two ears of a person. The binaural beat phenomenon was discovered in 1839 by H. W. Dove, a German experimenter. Generally, this phenomenon works as follows. When an individual receives signals of two different frequencies, one signal to each ear, the individual's brain detects a phase difference or differences between these signals. When these signals are naturally occurring, the detected phased difference provides directional information to the higher centers of the brain. However, if these signals are provided through speakers or stereo earphones, the phase difference is detected as an anomaly. The resulting imposition of a consistent phase difference between the incoming signals causes the binaural beat in an amplitude modulated standing wave, within each superior olivary nucleus (sound processing center) of the brain. It is not possible to generate a binaural beat through an electronically mixed signal; rather, the action of both ears is required for detection of this beat.

Binaural beats are auditory brainstem responses which originate in the superior olivary nucleus of each hemisphere. They result from the interaction of two different auditory impulses, originating in opposite ears, below 1000 Hz and which differ in frequency between one and 30 Hz. For example, if a pure tone of 400 Hz is presented to the right ear and a pure tone of 410 Hz is presented simultaneously to the left ear, an amplitude modulated standing wave of 10 Hz, the difference between the two tones, is experienced as the two wave forms mesh in and out of phase within the superior olivary nuclei. This binaural beat is not heard in the ordinary sense of the word (the human range of hearing is from 20-20,000 Hz). It is perceived as an auditory beat and theoretically can be used to entrain specific neural rhythms through the frequency-following response (FFR)—the tendency for cortical potentials to entrain to or resonate at the frequency of an external stimulus. Thus, it is theoretically possible to utilize a specific binaural-beat frequency as a consciousness management technique to entrain a specific cortical rhythm.

When signals of two different frequencies are presented, one to each ear, the brain detects phase differences between these signals. Under natural circumstances a detected phase difference would provide directional information. The brain processes this anomalous information differently when these phase differences are heard with stereo headphones or speakers. A perceptual integration of the two signals takes place, producing the sensation of a third "beat" frequency. The difference between the signals waxes and wanes as the two different input frequencies mesh in and out of phase. As a result of these constantly increasing and decreasing differences, an amplitude-modulated standing wave—the binaural beat—is heard. The binaural beat is perceived as a fluctuating rhythm at the frequency of the difference between the two auditory inputs.

As a result, binaural beats are produced and are perceived by the brain as a result of the interaction of auditory signals within the brain. Such binaural beats are not produced outside of the brain as a result of the two audio signals of different frequencies. In a sense, the binaural beats are similar to beat frequency oscillations produced by a heterodyne effect, but occurring within the brain itself. However, the article discusses the use of such binaural beats in a strobe-type manner. In other words, if the brain is operating at one frequency, binaural beats of a fixed frequency are produced within the brain so as to entice the brain to change its frequency to that of the binaural beats and thereby change the brain state.

The binaural beat phenomenon described above also can create a frequency entrainment effect. If a binaural beat is within the range of brain wave frequencies, generally less than 30 cycles per second, the binaural beat will become an entrainment environment. This effect has been used to study states of consciousness, to improve therapeutic intervention techniques, and to enhance educational environments.

As the brain slows from beta to alpha to theta to delta, there is a corresponding increase in balance between the two hemispheres of the brain. This balanced brain state is called brain synchnony, or brain synchnonization. Normally, the brain waves exhibit asymmetrical patterns with one hemisphere dominant over the other. However, the balanced brain state offers deep tranquility, flashes of creative insight, euphoria, intensely focus attention, and enhanced learning abilities. Thus it is important for the creative activity of the individual to have a "correct" balance and communication between the brain halves.

SUMMARY OF THE INVENTION

A method and apparatus is disclosed to balance the brain left side and the brain right side by using binaural beat. The disclosed apparatus comprises an electroencephalographic (EEG) system to measure the brain left and right electrical signals, an audio generator to generate a binaural beat to compensate for the unbalanced EEG frequencies. The disclosed method includes measuring the brain wave frequency spectrum of the individual, selecting the frequency exhibiting imbalanced behavior, and generating a binaural beat of that frequency.

The procedure depends upon the particular situation. The binaural beat can be continuous or intermitten. The desired frequency can be maintained for some predetermined period of time, after which a new desired frequency can be determined. Another possibility would be to take the user to a rest frequency between sessions. Another possibility would be to generate no signal at all for a period of time. The binaural beat can start at a higher or lower frequency and then moves toward the desired frequency.

The binaural beat can be generated by applying two different frequencies to two ears. The applied frequencies can range from 50 Hz to 400 Hz. The amplitudes and waveforms of the audio frequencies can vary to achieve best results for different users.

A computer is preferably used in the present invention for controlling the equipment or to provide feedback between the brain wave measurement and the audio generation. The binaural beat can be generated through electronic synthesizer or a frequency generator. The measurement of the brain wave is preferably by the use of an EEG equipment, but any other brain scan equipment can be used.

The present invention first measures the left and right brain wave frequencies of the individual by use of electroencephalographic (EEG) to determine the brain wave imbalance, then entraining the brain wave frequency of the individual at a chosen imbalanced brain wave frequency to improve the brain wave balance at that particular frequency. The present invention uses the EEG feedback to ensure of the proper balancing treatment.

DETAILED DESCRIPTION OF THE INVENTION

Figure 1:
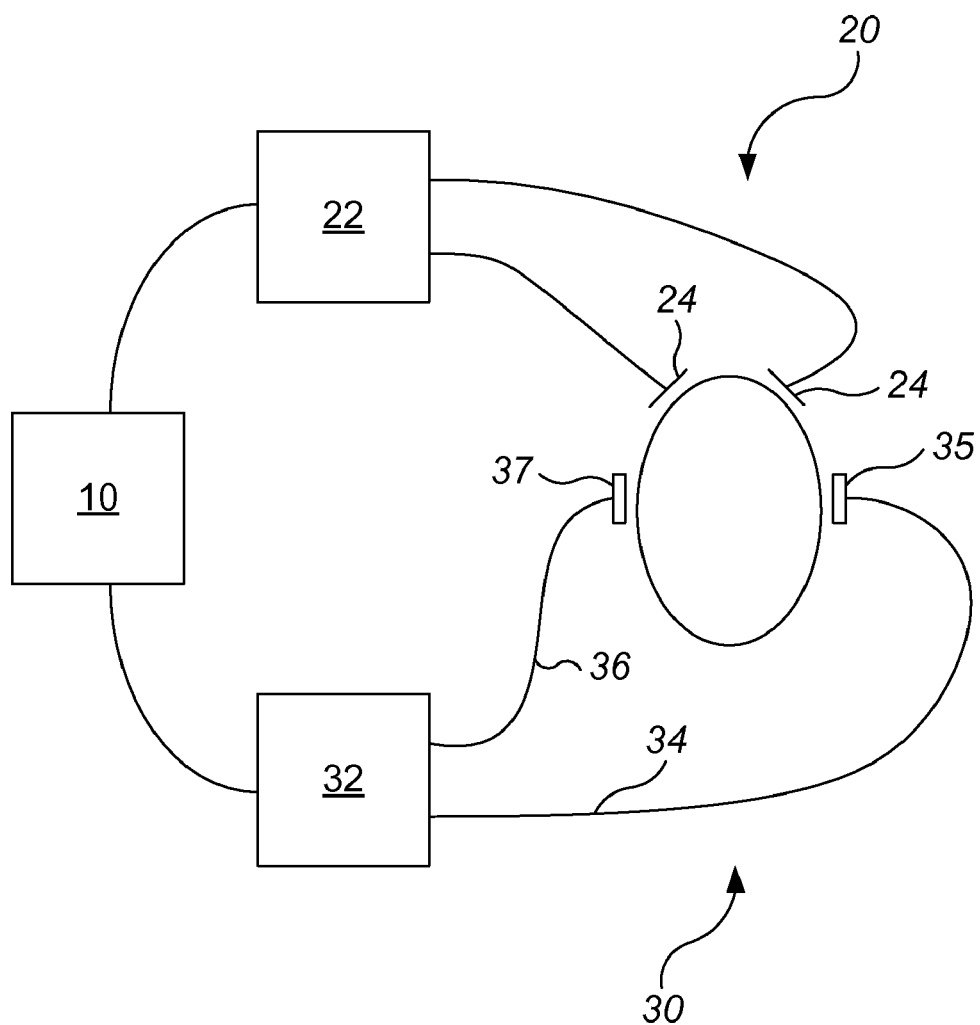
FIG. 1 shows an embodiment of the present invention apparatus.

Deep relaxation technique combined with synchronized rhythms in the brain has been proven to provide the ability to learn over five times as much information with less study time per day, and with greater long term retention, and is credited to alpha wave production.

The left brain half is verbal, analytical and logical in its functioning, while the right is musical, emotional and spatially perceptive. The left brain hemisphere thinks in words and concepts, and the right thinks in pictures, feelings and perceptions. In a normal brain, a spontaneous shift in balance occurs between left and right, depending on what one is doing. When one is reading, writing and speaking, the left half will be more active than the right. On the other hand, when one is listening to music or is engaged in visual spatial perception, then the right half is most active.

By calculating the ratio between the amount of alpha waves in the right and left brain hemispheres, an expression for the balance between the brain halves is obtained, the so-called R/L ratio. If there is exactly the same amount of alpha waves in the right and left brain hemispheres, the R/L ratio will be 1.00. If there is more alpha in the right brain half, the R/L ratio will be more than 1.00, and vice versa, the R/L ratio will be less than 1.00 if there is more alpha in the left brain half.

In most people during rest with closed eyes, the RIL ratio is normally slightly above 1.00. This is probably due to our culture's emphasis on the functions of the left brain half. During deep relaxation, however, a balance of 1.00 between the brain halves is approached.

Thus the present invention discloses an apparatus and method to achieve the brain balance. The brain balance can have the RIL ratio to be around 1.00, but can be as low as 0.9 or high as 1.10, depending on the need of the users. The present invention also provides a feedback mechanism by brain signals measurements (such as by using EEG electrodes) to ensure the proper treatment. Further, the brain is a living organism, and thus is capable of self-correcting. The present invention can also provide the initial push toward brain balancing. By nudging toward brain balancing, the brain can learn to be balanced by itself without the need of any external stimuli.

Shown in FIG. 1 is the present invention apparatus, comprising a computer 10 for controlling the equipment, an EEG system 20 to measure the brain wave spectrum, and a binaural beat system 30 to generate a binaural beat. The EEG system comprises an amplifier 22 and a plurality of electrodes 24 attached to the scalp of the user. The number of electrodes 24 is even and at least 2, one for each half of the brain, but can be as many as 20 or 40. The electrodes 24 and amplifier 22 can communicate with the computer 10. The binaural beat system 30 comprises a generator 32 to generate a first signal at a first frequency on a first channel 34 and a second signal at a second frequency on a second channel 36. The frequency difference between the first and second signals creates the binaural beat corresponding to a chosen imbalance brain wave frequency. First channel 34 send the first signal to one ear of the user through an earphone 35, and second channel 36 send the second signal to the other ear of the user through an earphone 37. The binaural beat system 30 is responsive to the computer 10. There are optional devices such keypad, keyboard, mouse and display for conventional input and output devices, and volume, waveform, and balance controls for adjusting to the individual user and the purpose of the use.

In another embodiment of the invention, either or both the electrodes 24 and the earphones 35, 37 are wireless, and communicate with the amplifier 22 and the signal generator 32 wirelessly. The electrode 24 can be a modified eyewear handle, the cover part of the earphone, the outer part of the earphone, or the muffle of the earphone. The brain signals measurement can be any electromagnetic emission measurement device, or any electrical emission measurement device (such as EEG device). The output of the measuring device is the brain wave emission, typically a spectrum curve, which is a function of amplitude or phase with respect to frequency. A Fourrier transform to convert the emission measurement to a frequency spectrum can be added if the output of the measurement device is not in frequency spectrum form. Within the whole spectrum of the brain wave emissions, the imbalanced frequencies that exhibiting imbalanced behaviors, such as a difference in amplitude or phase between the left and right sides of the brain.

Generally, the binaural beat frequency that the brain can detect, ranges from approximately 0 to 100 Hz. The ear has the greatest sensitivity at around 1000 Hz. However, this frequency is not pleasant to listen to, and a frequency of 100 Hz is too low to provide a good modulation index. Thus the frequencies between 100 Hz and 1000 Hz are normally used for binaural beat, and preferably between 100 Hz and 400 Hz. Typically, the frequency of 200 Hz is a good compromise between sensitivity and pleasing sounds.

Thus according to the present invention, a constant frequency of 200 Hz audio signal can supplied to one ear (for example, the left ear) and another audio signal having a frequency which ranges from 300 Hz to 200 Hz is applied to the other ear (for example, the right ear). As a result, binaural beats at 0-100 Hz are produced in the brain. The audio signals can be toggled, meaning the constant frequency can be applied to the right ear and the varied frequency applied to the left ear. Further the toggle can happen at a fast rate. This toggle rate can help to maintain the attention span of the brain during the binaural beat generation and might allow the user to perceive the signal moving back and forth between the left and right ears. Further, the left and right ear signals can have different time delay or phase differences since, for low frequencies of this nature, the time delay or phase difference between the left and right signals could produce a greater effect than the relative amplitude to the brain. The time delay could be up to a few seconds and the phase difference can be anywhere from 0 to 360°.

The above audio signals can be produced in a plurality of ways. For example, an audio signal generator can be used to produce the audio signals and listened to through headphones. The audio signal can be computer generated. A computer program can be written to produce the required sound. Alternatively, analog operational amplifiers and other integrated circuitry can be provided in conjunction with a set of headphones to produce such audio signals. These signals may be recorded on a magnetic tape which the person listens to through a set of earphones. Headphones are necessary because otherwise the beat frequency would be produced in the air between the two speakers. This would produce audible beat notes, but would not produce the binaural beats within the brain.

The binaural beat can have various waveforms such as square, triangular, sinusoidal, or the various musical instruments. It is known that sound may be defined by its frequency, amplitude, and wave shape. For example, the musical note A has the frequency of 440 Hz, and the amplitude of that note is expressed as the loudness of the signal. However, the wave shape of that note is related strongly to the instrument used. An A played on a trumpet is quite different from an A played on a violin.

The present invention employs the EEG signals feedback to ensure proper application of the binaural beat. First, a brain frequency spectrum of an user is obtained through the EEG electrodes and EEG amplifier. From the spectrum, imbalanced frequencies are observed. The user then selects an imbalanced frequency to address. The brain frequencies are related to the human consciousness through various activities and enhancements such as better learning, better memory retention, better focus, better creativity, better insight, or just simply brain exercise, and thus instead of choosing a frequency, the user can just choose a desired enhancement. Then a binaural beat is applied using the selected frequency by audio inputs.

There are various brain balancing procedure. For example, the binaural beat can be continuous or intermitten. The binaural beat at the correcting or desired frequency can be maintained for some predetermined period of time, after which a new correcting or desired frequency can be determined. Another possibility would be to take the user to a rest frequency between sessions. Another possibility would be to allow the user to rest between sessions, e.g. generating no signal at all for a period of time. The amplitude and waveform of the applied frequencies can be constant, selected by the user, or vary. The binaural beat can start at the correcting or desired frequency, or can start at a higher or lower frequency and then moves toward the correcting or desired frequency. The binaural beat can phase lock onto a certain brain wave frequency of the person and to gently carry down to the desired frequency. The scanning or continuously varying frequency can be important since the different halves generally operate at different brain frequencies. This is because one brain half is generally dominant over the other brain half. Therefore, by scanning at different frequencies from a higher frequency to a lower frequency, or vice versa, each brain half is locked onto the respective frequency and carried down or up so that both brain halves are operating synchronously with each other and are moved to the desired frequency brain wave pattern corresponding to the chosen state. Synchronized brain waves have long been associated with meditative and hypnogogic states, and audio with embedded binaural beats has the ability to induce and improve such states of consciousness. The reason for this is physiological. Each ear is "hard-wired" to both hemispheres of the brain. Each hemisphere has its own olivary nucleus (sound-processing center) which receives signals from each ear. In keeping with this physiological structure, when a binaural beat is perceived there are actually two standing waves of equal amplitude and frequency present, one in each hemisphere. So, there are two separate standing waves entraining portions of each hemisphere to the same frequency. The binaural beats appear to contribute to the hemispheric synchronization evidenced in meditative and hypnogogic states of consciousness. Brain function is also enhanced through the increase of cross-collosal communication between the left and right hemispheres of the brain.

How can audio binaural beats alters brain waves? We know that the electrical potentials of brain waves can be measured and easily quantified, such as EEG patterns. As to the second question raised in the above paragraph, audio with embedded binaural beats alters the electrochemical environment of the brain. This allows mind-consciousness to have different experiences. When the brain is entrained to lower frequencies and awareness is maintained, a unique state of consciousness emerges. This state is often referred to as hypnogogia "mind awake/body asleep." Slightly higher-frequency entrainment can lead to hyper suggestive states of consciousness. Still higher-frequency EEG states are associated with alert and focused mental activity needed for the optimal performance of many tasks.

Synchronizing the left and right hemispheres allows the left brain to recognize the black and white words and smoothly transfer the meaning in color, motion, emotion etc. to the right brain to be converted into understandable thoughts that are easy to remember.

The present invention can affect various types of balancing brain activity.

In all of the embodiments which will be discussed hereinafter in more detail, it is essential that an audio signal be produced in which the frequency thereof or binaural beats produced thereby passes through the then operating brain-wave frequency of the person in order to lock onto and balance the brain-wave frequency. It is known that telling a stressed person to relax is rarely effective. Even when the person knows that he must try to relax, he usually cannot. Meditation and other relaxation methods seldom work with this type of person. Worrying about being stressed makes the person more stressed, producing a vicious cycle.

Another type is to raise the brain wave frequency, and particularly, to increase the performance of the person, for example, in sporting events. In this mode, both ears of the person are supplied with the same audio signal having a substantially continuously varying frequency which varies, for example, from 20 Hz to 40 Hz, although the signals are amplitude and/or phase modulated. It is believed that, if the brain wave frequency of the person is less than 20 Hz, the brain will phase lock onto audio signals of the same frequency or multiples of the same frequency. Thus, even if the brain is operating at a 10 Hz frequency rate, when an audio signal of 20 Hz is supplied, the brain will be phase locked onto such a signal and will be nudged up as the frequency is increased. Without such variation in frequency of the audio signal, the brain wave frequency will phase lock thereto, but will not be nudged up. Preferably, the audio signal changes from 20 Hz to 40 Hz in a time period of approximately 5 minutes and continuously repeats thereafter so as to nudge the brain frequency to a higher frequency during each cycle.

In view of the foregoing, it is one object of the invention to provide a method of inducing states of consciousness by generating stereo audio signals having specific wave shapes. These signals act as a carrier of a binaural beat. The resulting beat acts to entrain brain waves into unique waveforms characteristic of identified states of consciousness.

As will be discussed below, different regions of the brain produce distinct electrical waveforms during various physical, mental, and emotional states of consciousness. In the method of the invention, binaural beat audio wave shapes are made to match such particular brain waves as they occur during any mental physical, and emotional human condition of consciousness. Thus, it is possible to convert waveforms from specific brain regions, as well as complete brain surface electrical topography.

Many times the brain wave patterned is locked, and thus a disruption of the locked brain is necessary to bring the brain back to the synchonizing state, and to re-establish the biological systems flexibility. The present method uses the EEG measurements to identify regions of the brain that need work, and the binaural beat technique to exercise the brain. The locations of the EEG electrodes can be anywhere near the center of the forehead which are near the dominant brain wave frequency.

The EEG measures the brain wave with different frequencies to establish the frequency spectrum. The frequency spectrum might also be obtained from a transformation of the brain wave frequency measurements. Such a transform may include, but not be limited to, a compression, expansion, phase difference, statistical sampling or time delay from the brain wave frequency.

It is preferred that the working time be between one second and one hour. It is more preferred that the time be between 1 and 30 minutes. It is even more preferred that the time is between 1 minute and 10 minutes.

What is claim is:

1. A method to balance the brain left and right side of a user using binaural beat, the method comprising
   a) measuring a left electromagnetic emission from the left side brain of the user;
   b) measuring a right electromagnetic emission from the right side brain of the user;
   c) using a processor, selecting a correcting frequency using the left electromagnetic emission and the right electromagnetic emission, wherein the correcting frequency is a frequency in the vicinity of an imbalanced frequency exhibiting an imbalance behavior;
   d) generating a binaural beat of the correcting frequency; and
   e) applying the binaural beat to the left and right ears of the user.

2. A method as in claim 1, further comprising a step of generating a left brain frequency spectrum from the left electromagnetic emission, and a right brain frequency spectrum from the right electromagnetic emission.

3. A method as in claim 1 wherein the binaural beat is continuous or intermittent.

4. A method as in claim 1 wherein the binaural beat has different time delay or phase differences.

5. A method as in claim 1, further comprising a step of repeating steps c) to e) while moving the correcting frequency toward the imbalanced frequency.

6. A method as in claim 1 wherein the correcting frequency is higher than the imbalanced frequency.

7. A method as in claim 1 wherein the correcting frequency is lower than the imbalanced frequency.

8. A method as in claim 1 wherein the binaural beat for the correcting frequency is maintained for a predetermined period of time.

9. A method as in claim 1, further comprising a step of repeating steps c) to e) until a balanced frequency that exhibits balanced behavior is selected, wherein the balanced frequency is a frequency with similar magnitude between the left side emission and the right side emission.

10. A method as in claim 1, further comprising a step of repeating steps c) to e) while selecting another correcting frequency.

11. A method as in claim 10 further comprising a step of generating a rest frequency between two correcting frequencies.

12. A method as in claim 11 wherein the rest frequency is a frequency not in the vicinity of a frequency exhibiting imbalance behavior.

13. A method as in claim 10 further comprising a step of generating a rest period between two correcting frequencies, wherein there is no binaural beat during the rest period.

14. A method as in claim 1 wherein the correcting frequency is the imbalanced frequency.

15. A method as in claim 1 wherein the imbalanced frequency is a frequency with different magnitude or different phase between the left side emission and the right side emission.

16. A method as in claim 1 wherein the binaural beat is generated from two different frequencies to two ears, the two different frequencies ranging from 40 Hz to 400 Hz.

17. A method as in claim 1 wherein the binaural beat is generated from two different frequencies to two ears, the binaural beat frequency ranging from 0.1 Hz to 40 Hz.

18. A method as in claim 1 further comprising the step of repeating the steps a) to e) until a predetermined improved balancing is achieved.

19. A method to balance the brain left and right side of a user using binaural beat, the method comprising
   measuring a left electrical brain wave spectrum from the left side brain of the user;
   measuring a right electrical brain wave spectrum from the right side brain of the user;
   using a processor, selecting a correcting frequency, wherein the correcting frequency is the frequency in the vicinity of a frequency with different magnitude or different phase between the left side spectrum and the right side spectrum;
   generating a binaural beat of the correcting frequency; and
   applying the binaural beat to the user's left and right ears.

* * * * *